(12) United States Patent
Mernoe

(10) Patent No.: US 7,998,116 B2
(45) Date of Patent: *Aug. 16, 2011

(54) MEDICINE DISPENSING DEVICE

(75) Inventor: Morten Mernoe, Charlottenlund (DK)

(73) Assignee: Asante Solutions, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/767,570

(22) Filed: Apr. 26, 2010

(65) Prior Publication Data

US 2010/0274192 A1 Oct. 28, 2010

Related U.S. Application Data

(63) Continuation of application No. 10/591,190, filed on Aug. 31, 2006, now Pat. No. 7,713,238.

(30) Foreign Application Priority Data

| Apr. 6, 2005 | (DK) | 2005 00483 |
| Apr. 14, 2005 | (DK) | 2005 05423 |
| Jun. 3, 2005 | (DK) | 2005 00817 |

Apr. 6, 2006 (WO) ................ PCT/DK2006/000195

(51) Int. Cl.
*A61M 37/00* (2006.01)

(52) U.S. Cl. ........................................ 604/131

(58) Field of Classification Search ................ 604/131, 604/151–155, 207–211, 174; 128/DIG. 1, 128/DIG. 12

See application file for complete search history.

(56) References Cited

U.S. PATENT DOCUMENTS 7,713,238 B2 * 5/2010 Mernoe .................. 604/131

* cited by examiner

*Primary Examiner* — Theodore J Stigell
(74) *Attorney, Agent, or Firm* — Fish & Richardson P.C.

(57) ABSTRACT

Some embodiments of a wearable, disposable medicine dispensing device may include a piston rod that is advanced to dispense medicine from the device. A rotational motor may be coupled to a drive mechanism so as to carry out a certain number of revolutions and thereby displace the piston rod by a desired distance. Such a device can be used in a method of dispensing liquid medicine.

15 Claims, 16 Drawing Sheets

US 7,998,116 B2

MEDICINE DISPENSING DEVICE

CROSS-REFERENCE TO RELATED APPLICATIONS

This application is continuation of U.S. patent application Ser. No. 10/591,190 (now U.S. Pat. No. 7,713,238) filed on Aug. 31, 2006 and entitled "An Actuator," which is a national stage application under 35 U.S.C. §371 that claims the benefit of PCT/DK2006/000195 (published as WO2006/105794) filed on Apr. 6, 2006 and entitled "An Actuator," which claims priority to the following Denmark patent applications: serial no. PA 2005 00483 filed on Apr. 6, 2005, serial no. PA 200 filed on Apr. 14, 2005, and serial no. PA 2005 00817 filed on Jun. 3, 2005. The entire contents of these prior applications are incorporated herein by reference.

SUMMARY OF INVENTION

The present invention relates to a method of dispensing liquid medicine comprising the steps of providing a wearable, disposable dispensing device comprising a syringe having a cylinder and a plunger displaceable in said syringe cylinder for pressing medicine out of said syringe cylinder and a drive mechanism connected to said plunger for displacing said plunger in said cylinder, and an electrical motor connected to a battery and to said drive mechanism for providing a rotary force to said driving mechanism for displacing said plunger, displacing said plunger a certain distance in connection with a cycle of said driving mechanism.

Methods of this type are known, wherein the electrical motor is controlled by a control means so as to carry out a certain number of revolutions for each cycle corresponding to the desired distance of displacement of the plunger.

In connection with such methods it is important that no more than the predetermined amount of medicine be dispensed per cycle as otherwise life threatening dosages may be dispensed.

When utilizing an electrical motor, a short circuit can entail that the motor does not stop after the predetermined number of revolutions or that the motor starts by itself.

Security means have been suggested to ensure that the predetermined dosage is not exceeded, for instance monitoring the amount of liquid dispensed per cycle or monitoring the displacement distance of the plunger or the amount of revolutions of the motor per cycle with interruption means being activated if the monitored elements exceed a certain value.

There exists a need for a simple and fail-safe method to avoid over-dosage of medicine. One main object of the invention is to meet this need.

According to the invention this object is achieved by the cycle comprising rotating said electrical motor in a first direction of rotation and subsequently rotating said electrical motor in the opposite direction of rotation.

Hereby, any short-circuit of the motor will not entail continued rotation of the motor in one direction with ensuing continued dispensing of medicine.

The invention furthermore relates to a wearable, disposable medicine dispensing device comprising:
- a syringe having cylinder and a plunger displaceable in the syringe cylinder for pressing medicine out of said syringe cylinder,
- a drive mechanism connected to said plunger for displacing said plunger in said cylinder, and
- an electrical motor connected to a battery and to said drive mechanism for providing a rotary force to said driving mechanism for displacing said plunger, and control means adapted for repeatedly reversing the direction of rotation of said electrical motor.

In a further aspect, the present invention relates to an actuator comprising:
- a rotational motor.
- one or more elongate, flexible elements such as a string, a filament, a strip, a ribbon and combinations thereof, said one or more elements being attached to said motor for rotation thereby and to a displaceable body, such that rotation of said motor twists said one or more elements and shortens the overall length thereof so that said displaceable body is displaced by the shortened element or elements.

Such an actuator according to the invention may be used in connection with medicine dispensing devices, but also in any application where a rotational force or movement is to be utilized to displace a body.

DESCRIPTION OF DRAWINGS

In the following the invention will be described more in detail in connection with two embodiments shown, solely by way of example, in the accompanying drawings, where.

DETAILED DESCRIPTION

Figure 1:
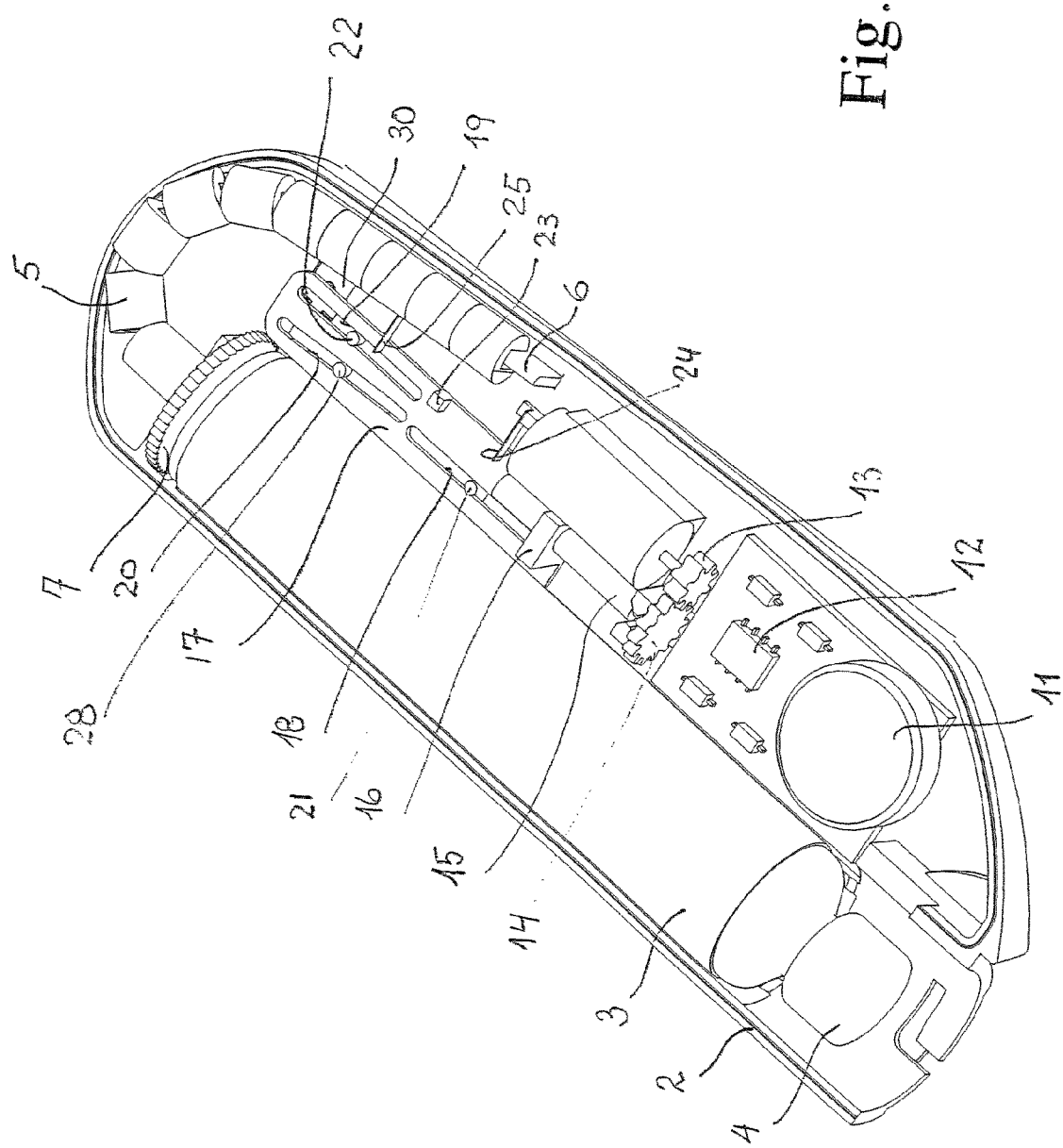
FIG. 1 shows a first embodiment of a device according to the invention seen in perspective and with the top part of the housing removed.
Figure 2:
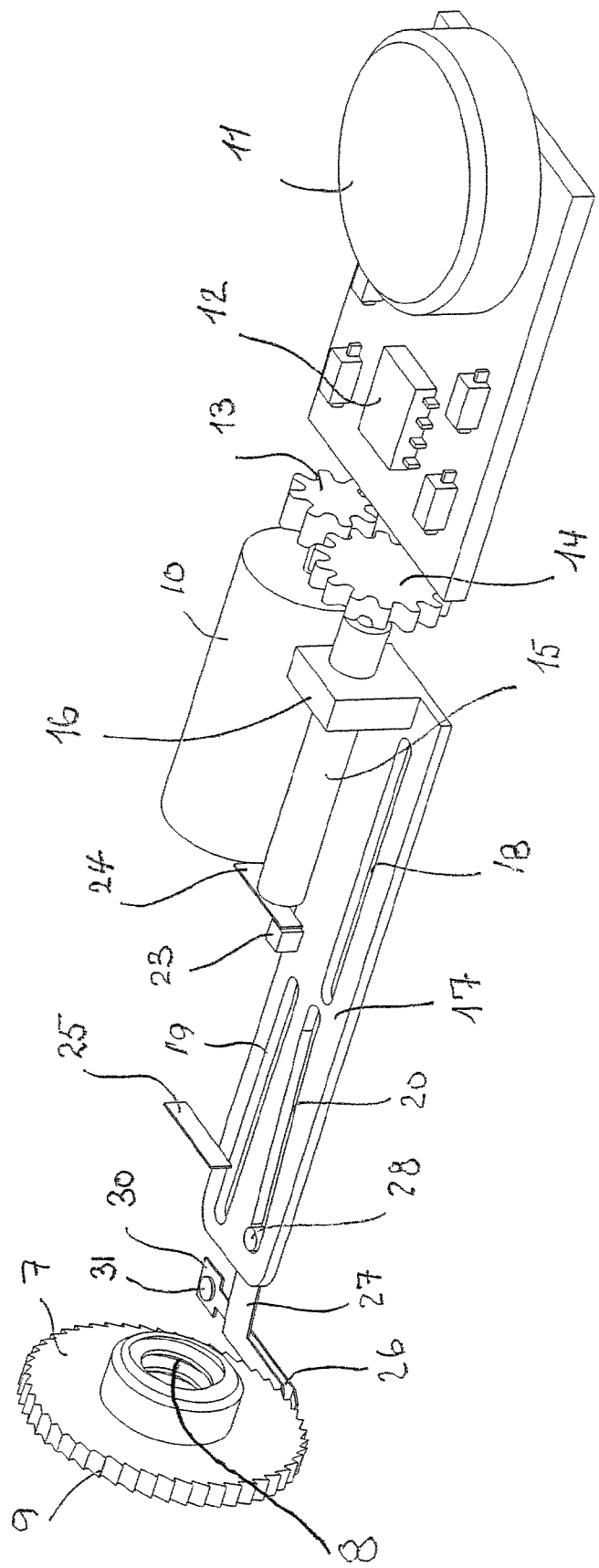
FIG. 2 shows a perspective view of the drive mechanism of the device according to the invention in FIG. 1.
Figure 3:
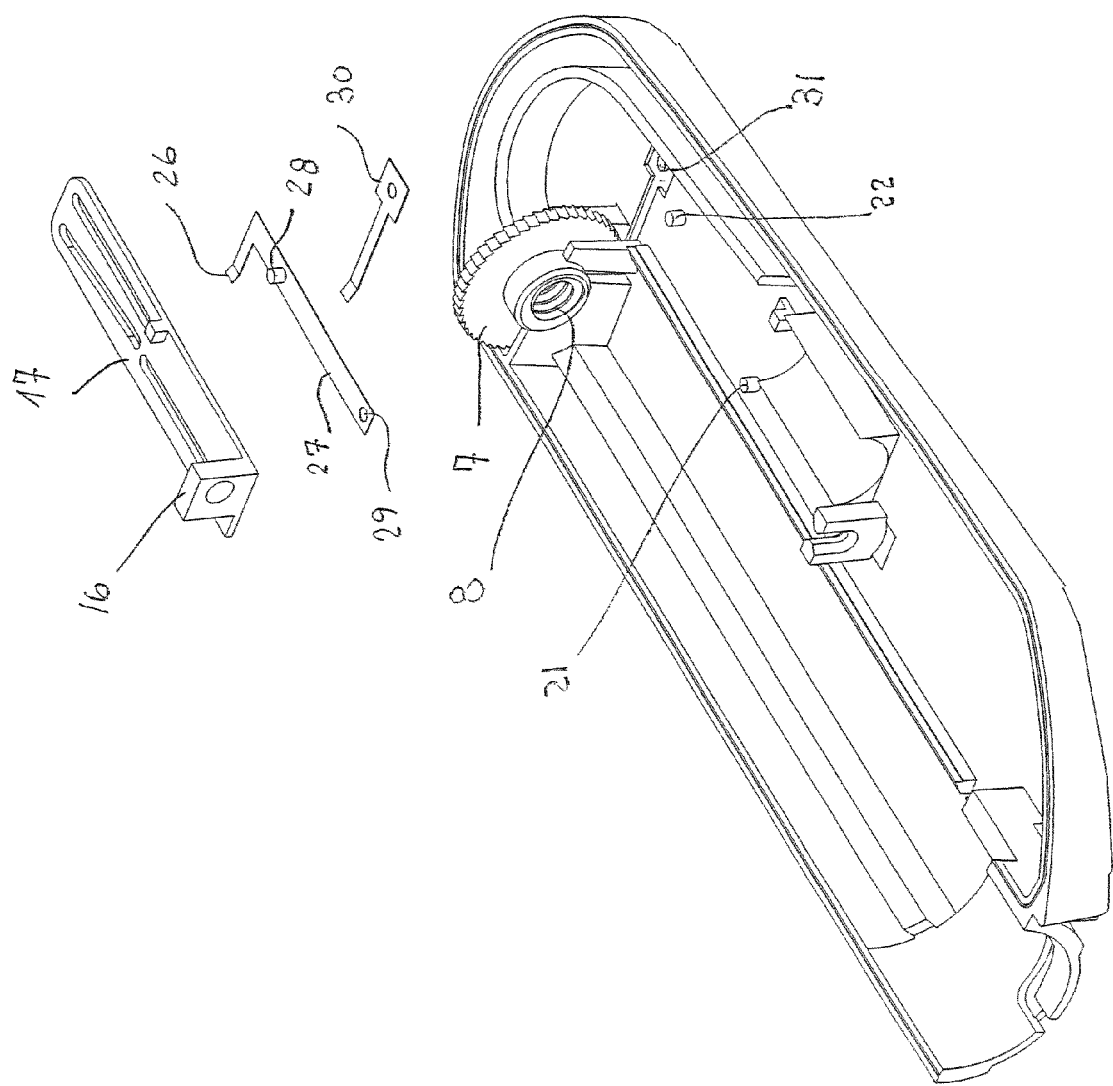
FIG. 3 is an exploded view of some of the drive mechanism elements of the device in FIG. 1, and FIGS. 4 and 5 are views corresponding to FIG. 2 with the drive mechanism in other positions.
Figure 4:
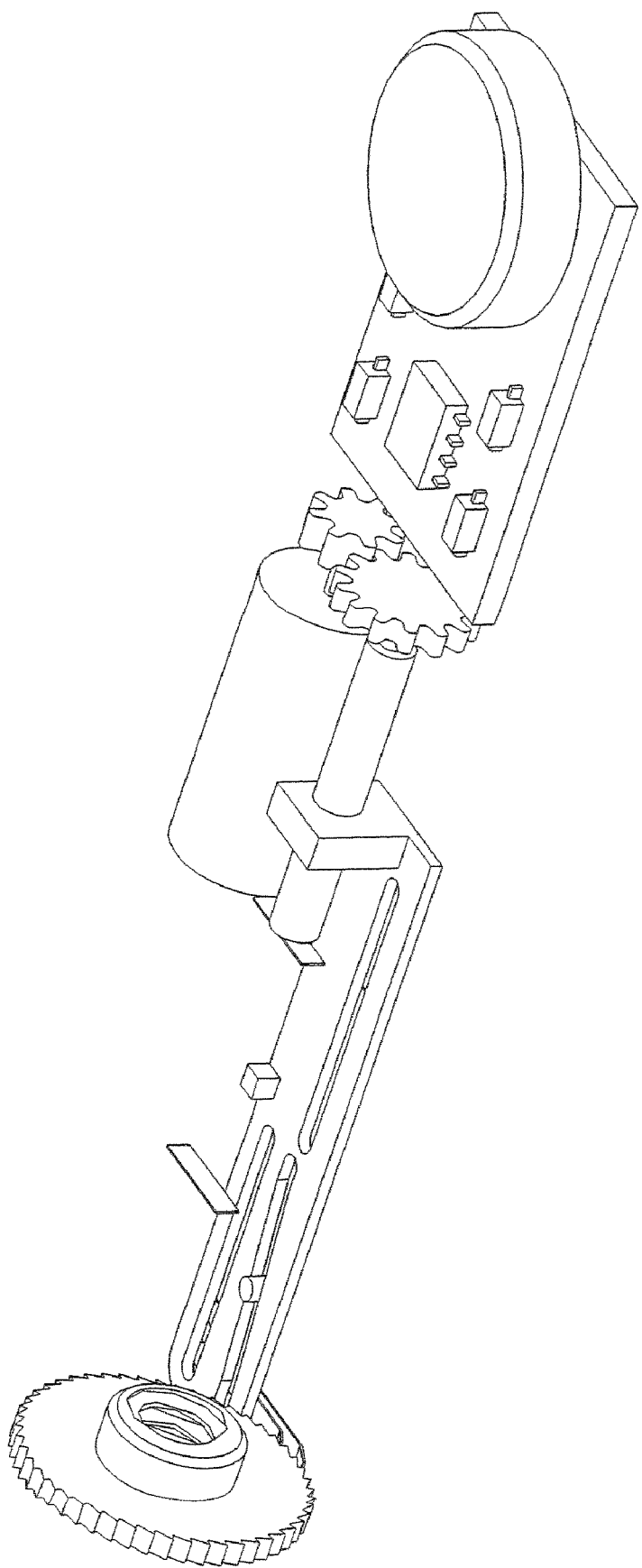
Figure 5:
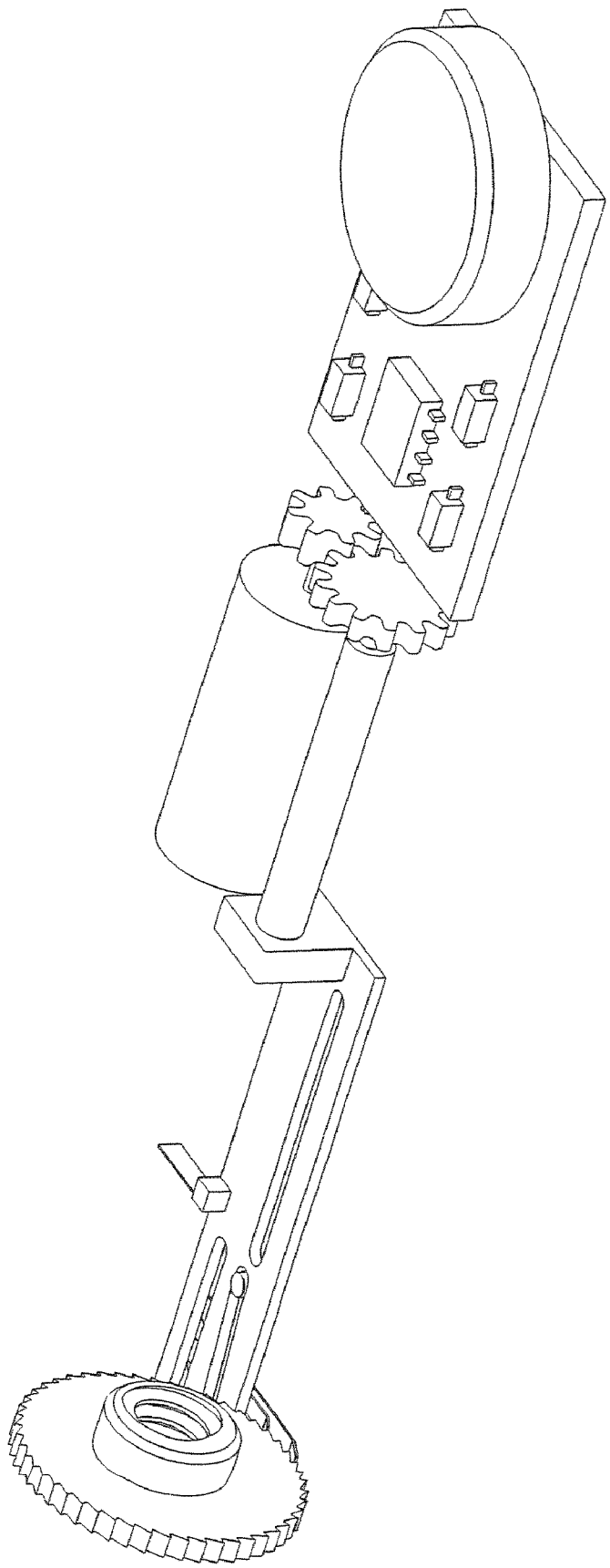
Figure 6:
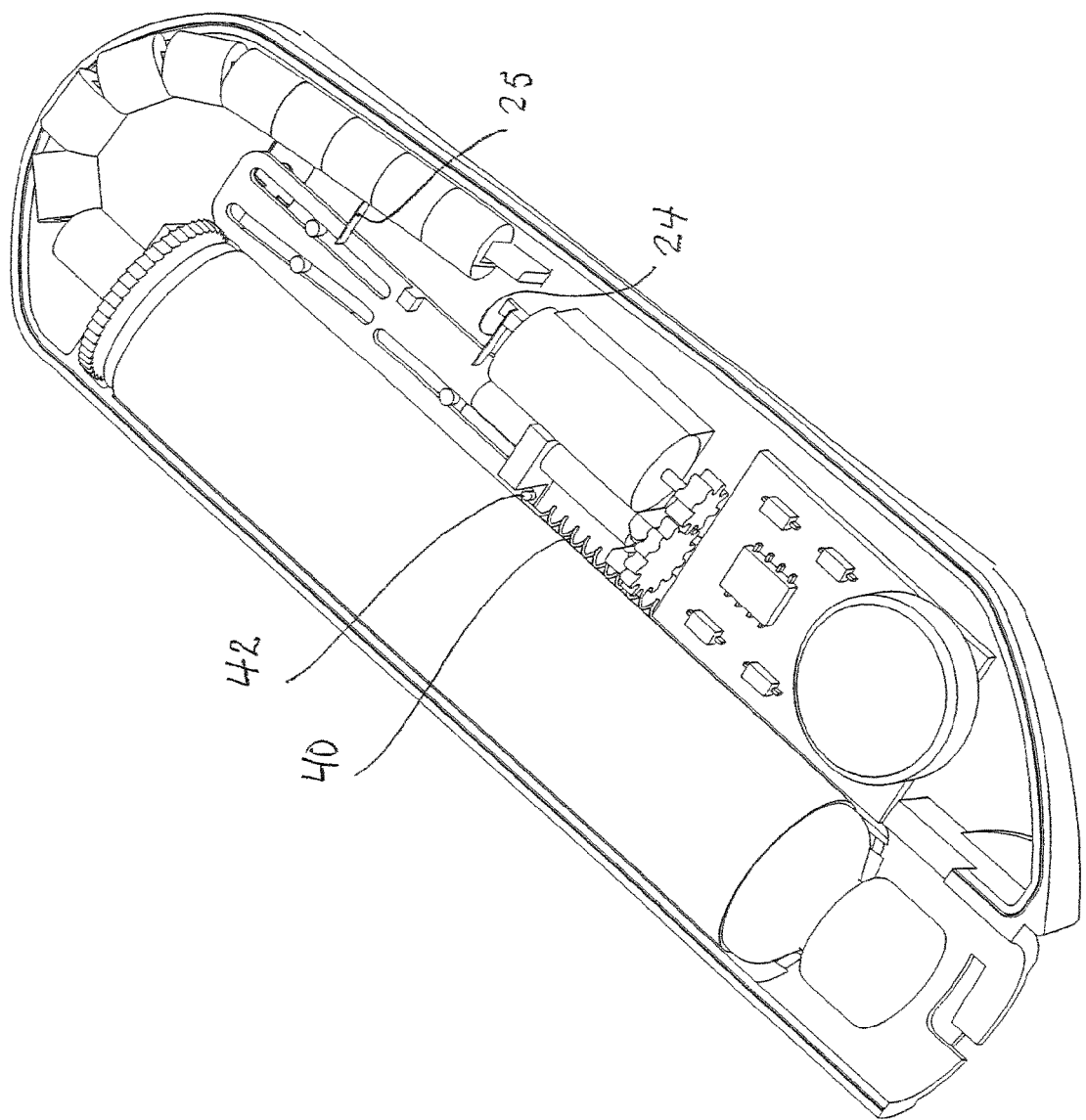
FIGS. 6-9 are views of a second embodiment of the device according to the invention corresponding to FIGS. 1, 2, 4 and 5, respectively.
Figure 7:
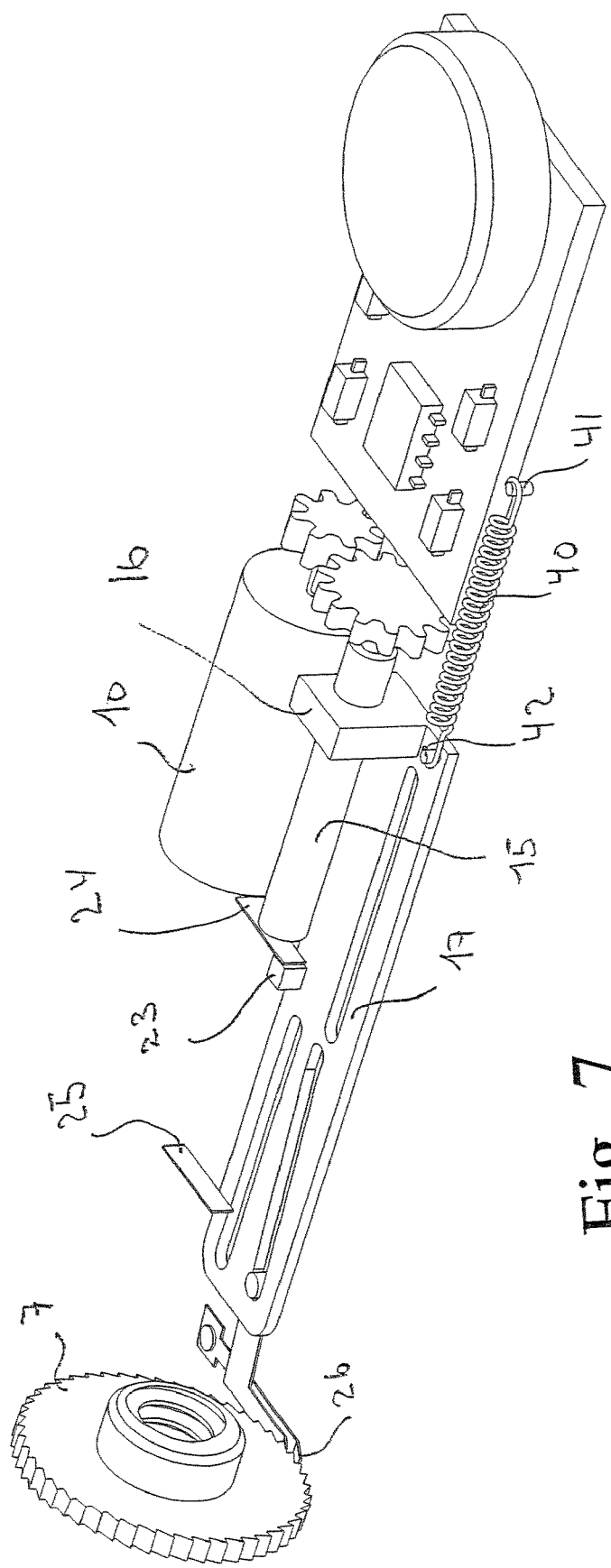
Figure 8:
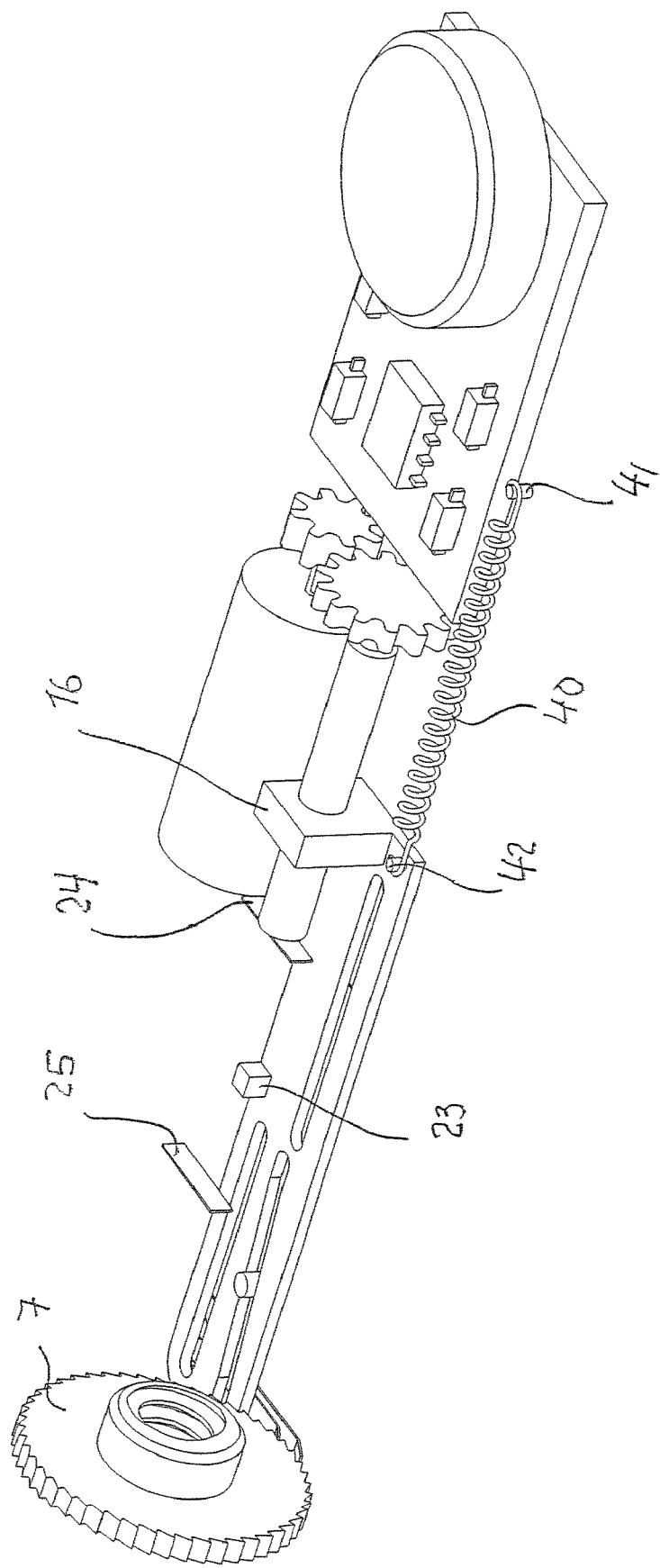
Figure 9:
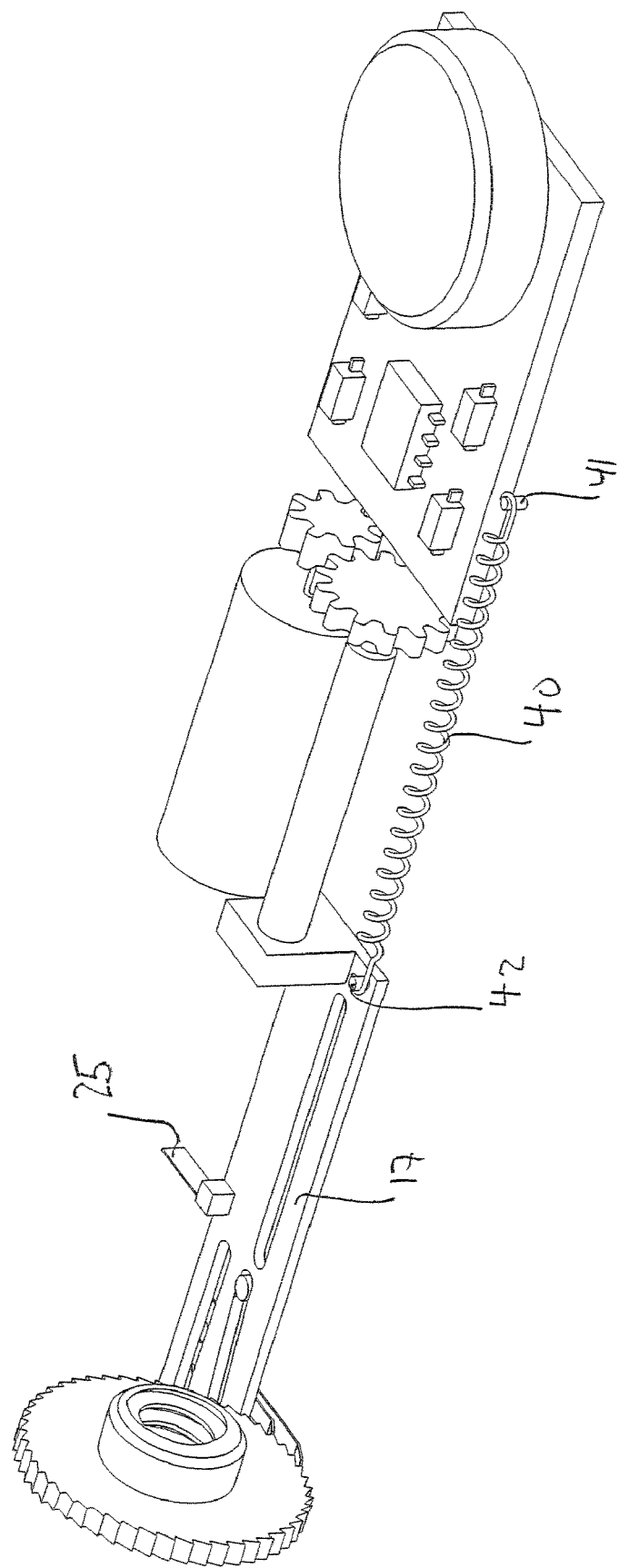
Figure 10:
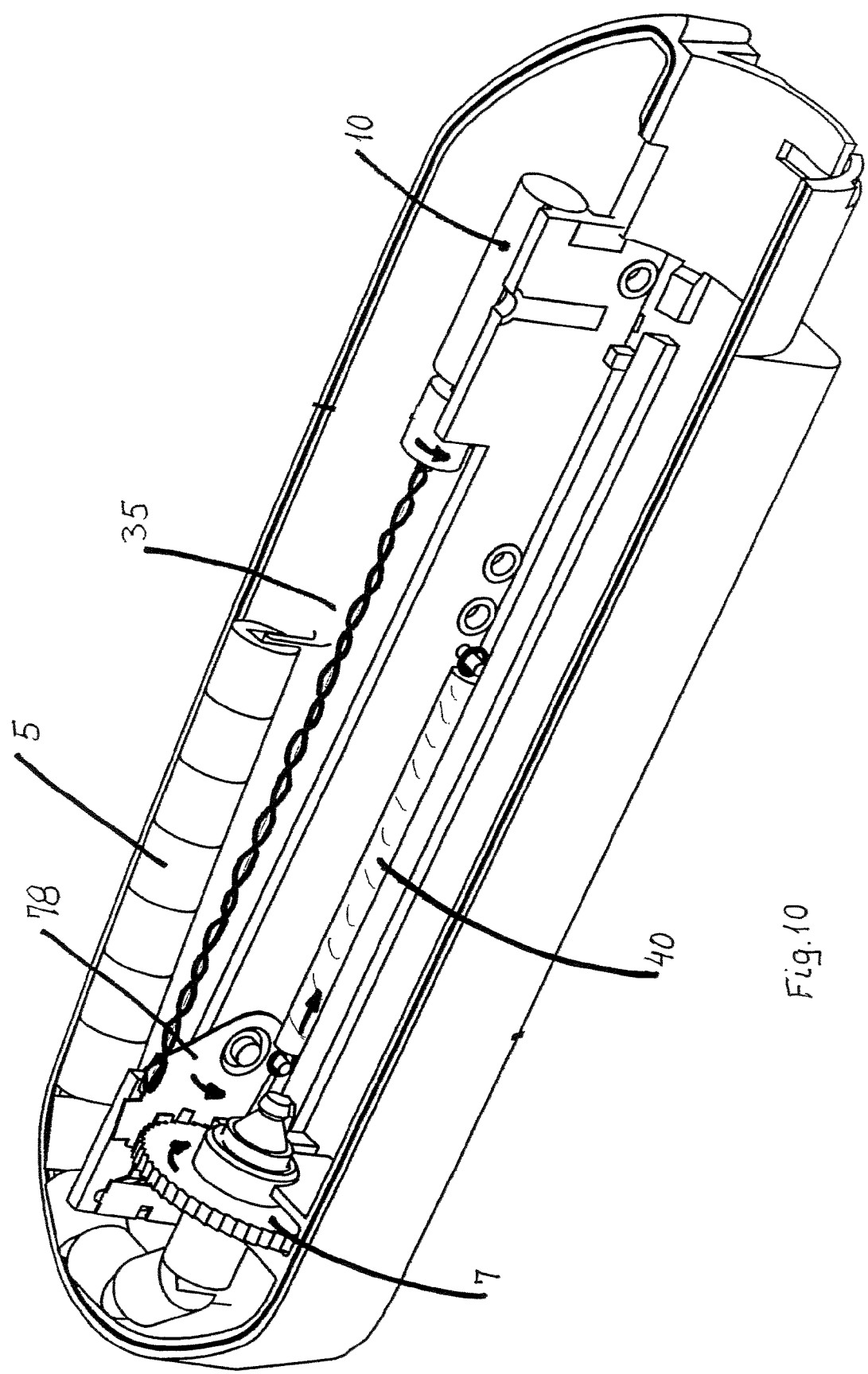
FIGS. 10-14 show a perspective view of a third embodiment of the device according to the invention in different sequential states during a first half cycle during rotation of the electrical motor in a first direction of rotation, FIGS. 15a, b and c are views of some of the drive mechanism elements of the device in FIGS. 10-14 in different states during the cycle.
Figure 11:
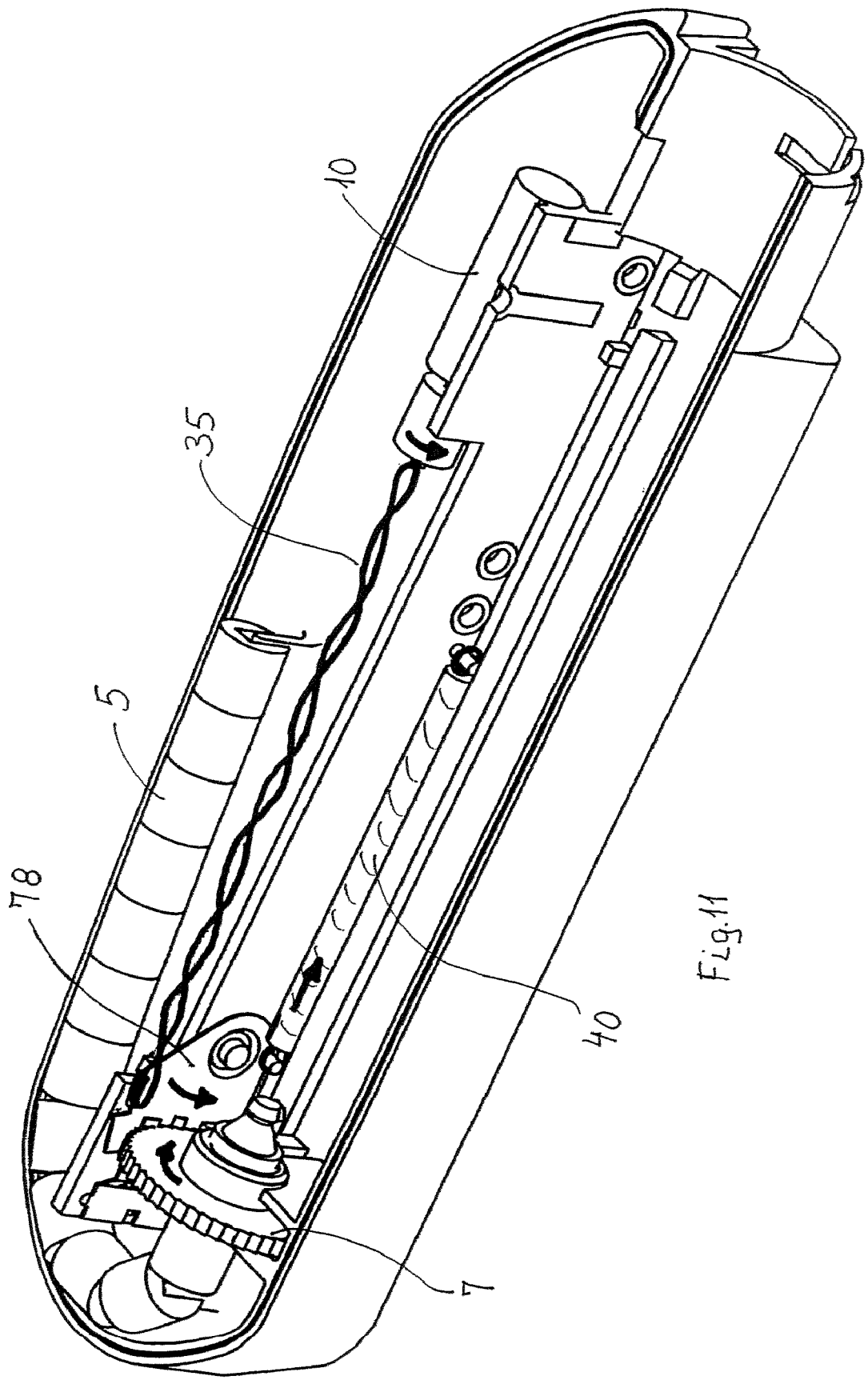
Figure 12:
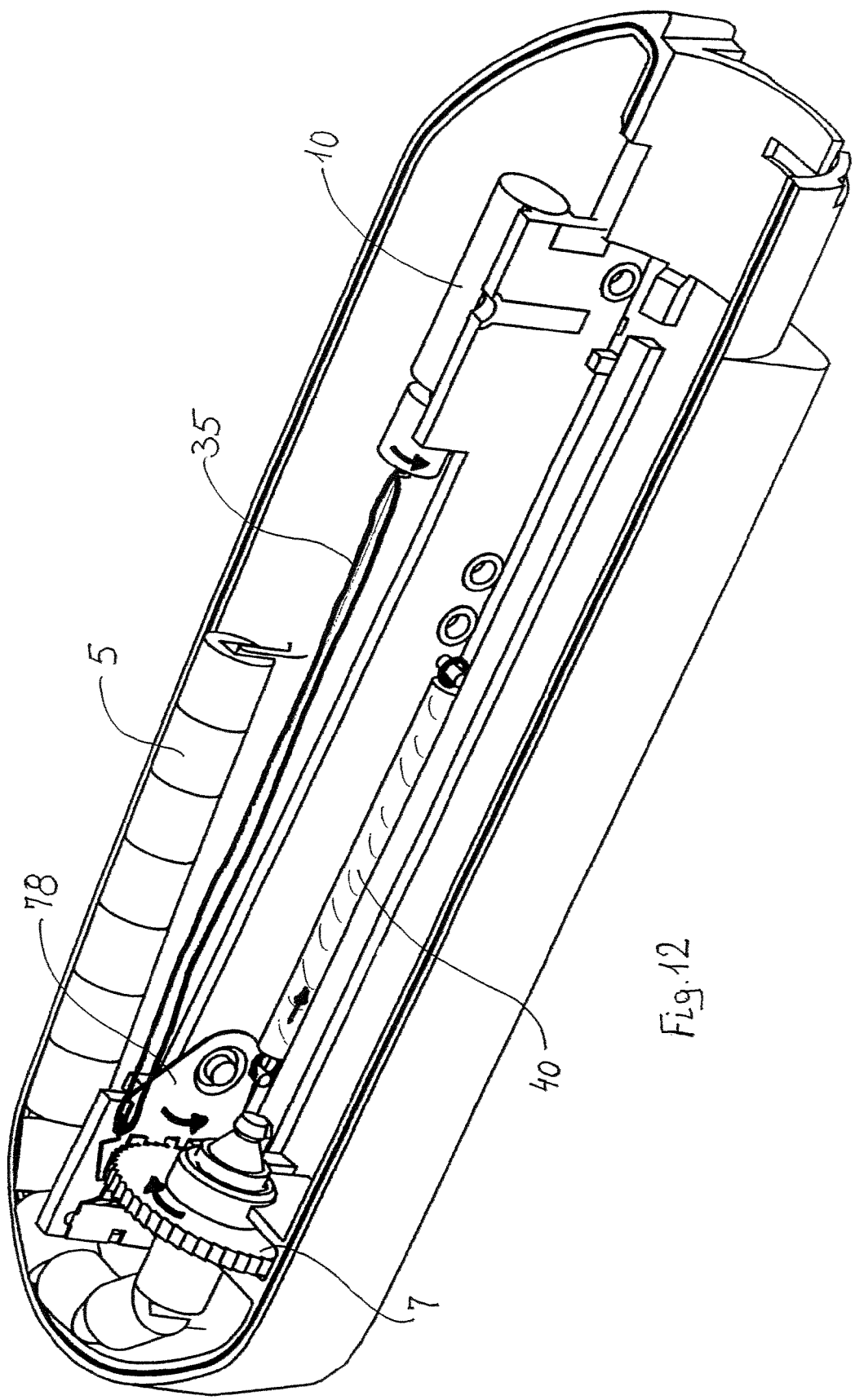
Figure 13:
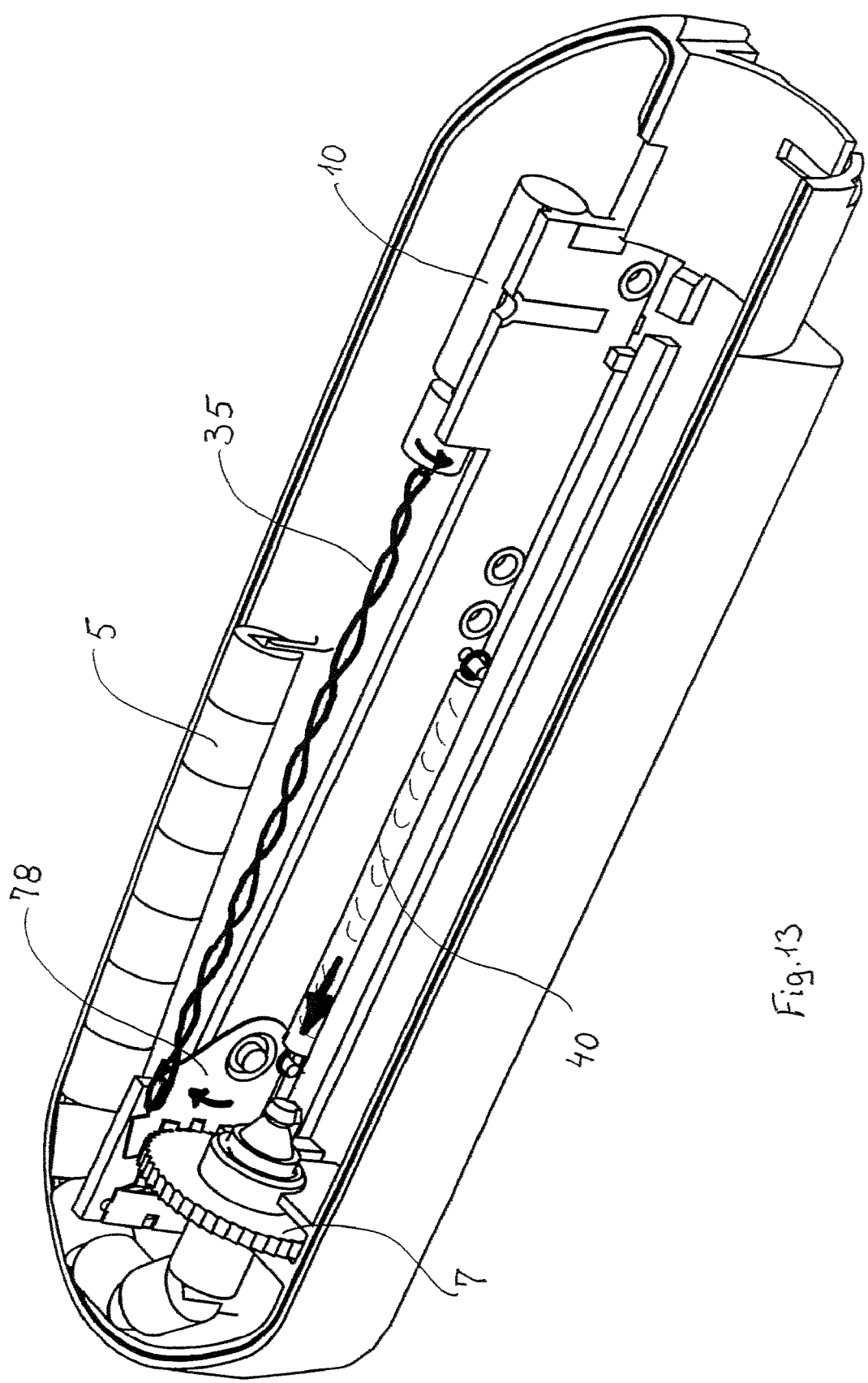
Figure 14:
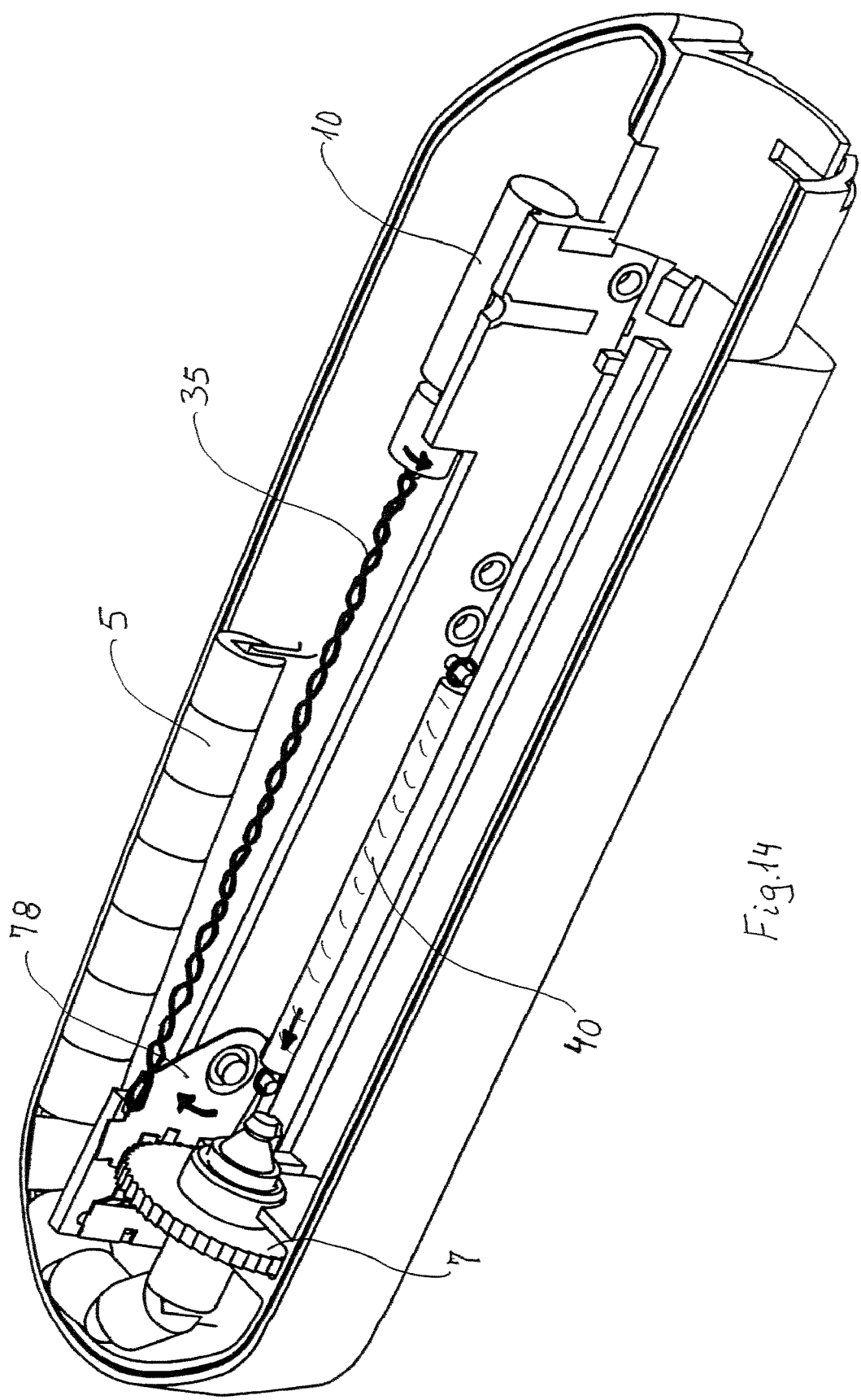
Figure 15:
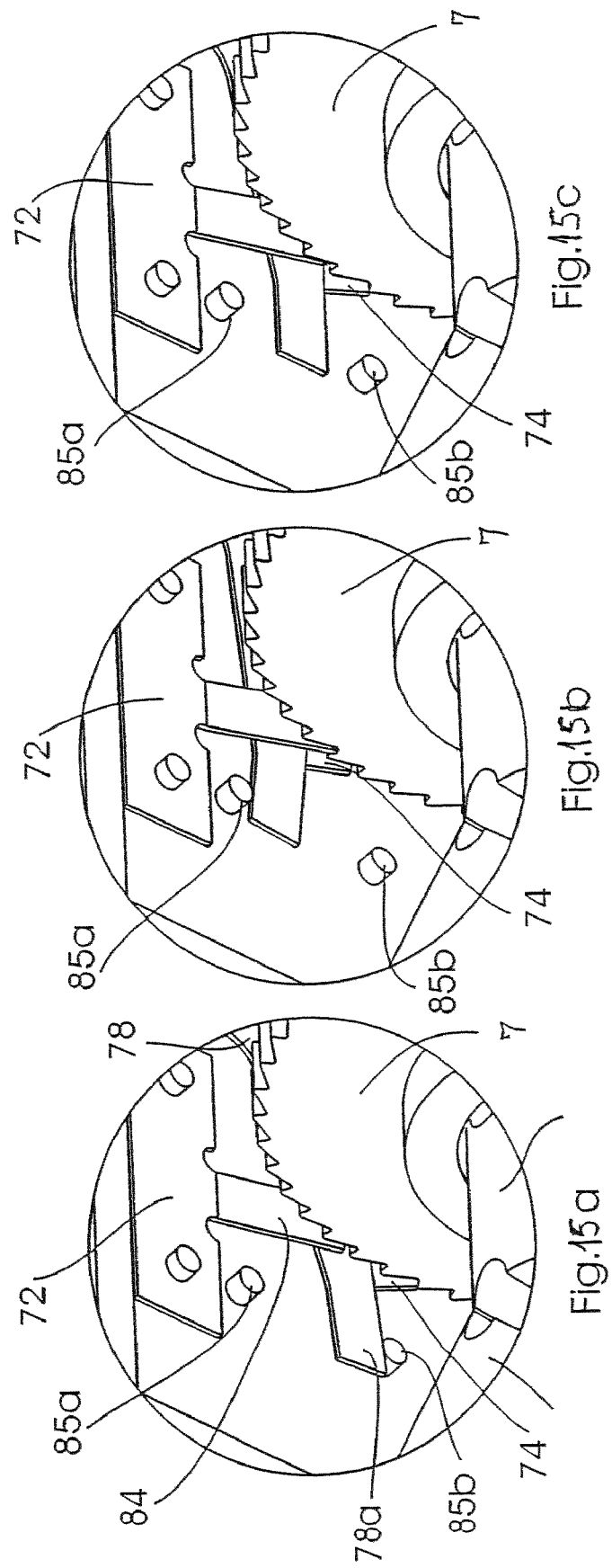

Referring now to FIGS. 1-5, a wearable disposable dispensing device for medicine referred to generally by the numeral 1 and of the type described in WO 2004/041330 and WO 2004/056412, the disclosure of which is hereby incorporated herein by reference, comprises a housing 2, where only the bottom half is shown for the sake of clarity, a cylindrical medicine container or carpule 3 having at one end a silicone body for receiving a catheter for dispensing medicine from the interior of the carpule to a human body and being open at the opposite end to receive a flexible piston rod 5 for displacing an internal not shown plunger or piston in the carpule 3 for forcing medicine out through a catheter needle assembly connected to the silicone body 4.

The flexible piston 5 is composed of segments hinged together and outwardly threaded guided by a rail 6 received in recesses in each of the segments of the rod 5. The not shown outward threads of the segments of the flexible piston rod 5 engage in a thread 8 of ratchet wheel 7 having teeth 9 along the periphery thereof. An electrical motor 10 electrically connected to a battery 11 and control means 12 is provided with a gear 13 meshing with a gear 14 attached to an outwardly threaded spindle or shaft 15 received in an inwardly threaded nut 16 attached a plate 17 provided with two slits 18 and 19, extending parallel to the axis of said spindle 15 and a third slit 20, extending at an angle to said axis. Two fixedly arranged pins 21 and 22 are received in the slits 18 and 19, respectively such that the pins serve as guides to the to and from displacement of the plate 17 by means of the spindle 15 when the electrical motor 10 rotates first in one directional rotation and thereafter in the opposite directional rotation.

A protuberance 23 is arranged on the plate 17 to co-operate with two end stop contacts 24 and 25 electrically connected to the control means 12 for reversing the direction of rotation of the electrical motor when the protuberance 23 contacts one of the end stop contacts 24 or 25. A pawl 26 is attached to a pivotable elongated body 27 having a pin 28 for being received in the oblique slit 20 and a hole 29 for receiving the pin 21 such that the body 27 is pivotable around the pin 21. A ratchet 30 is fixedly attached to the housing 2 by means of a pin 31 and is located so as to engage the teeth 9 of the ratchet wheel 7. The pawl 26 is displaceable from a retracted position where it does not engage the teeth 9 of the ratchet wheel 7 and in an engaged position in which it engages the teeth of the ratchet wheel and rotates the ratchet wheel in a clockwise direction.

The displacement of the pawl 26 between the two positions indicated above takes place by the linear displacement of the plate 17. When the plate 17 is displaced in the direction from the end stop contact 24 to the end stop contact 25, the oblique slit 20 urges the pin 28 of the elongated body 27 in a direction 10 away from the carpule 3 such that the elongated body 27 pivots around the pin 21 in a clockwise direction, whereby the pawl 26 is moved in towards its retracted position relative to the ratchet wheel 7. When the protuberance 23 on the plate 17 contacts the end stop contact 25, the directional rotation of the motor 10 is reversed and the plate 17 is displaced in the direction from the end stop contact 25 towards the end stop contact 24, whereby the oblique slit 20 forces the pin 28 towards the carpule 3, whereby the elongated body 27 is forced to rotate in a counterclockwise direction whereby the pawl 26 is brought into contact with one of the teeth 9 of the ratchet wheel and rotates the ratchet wheel in a clockwise direction, while the ratchet rides over one of the other teeth 9 for locking the ratchet wheel against rotation in the counterclockwise direction.

Thus, during one cycle of rotation in one direction and the opposite direction of the electrical motor 10, the ratchet wheel 7 will be advanced by one tooth corresponding to one displacement of the pawl 26 from the retracted position thereof to the engaged position thereof.

Referring now to FIGS. 6-9, in this embodiment a coil spring 40 is attached to a pin 41 fixedly attached to the housing 2 and a pin 42 fixedly attached to the plate 17.

When the plate 17 is moved in the direction from end contact 24 towards the end contact 25, the spring 40 is in tension, and when the plate 17 moves back in a direction from the end stop contact 25 towards the end stop contact 24 after reversion of the direction of rotation of the motor 10, the spring 40 will be relaxed and exert a force in the same direction as the motor 10 on the plate 17 and thus reinforcing the force available to rotate the ratchet wheel 7.

Referring now to FIGS. 10-15, the electrical motor 10 is electrically connected to a battery and control means and the axle of the motor is connected to a pair of twisted strings 35 or a band or similar device, which reduces its length when twisted and increases its length when untwisted, said length variation being provided by the rotation of the motor, i.e. the device is connected to the rotating axle of the motor at one end and connected to a pivotable body 78 at the opposite end. The pivotable body is provided with an extension 78a comprising a pawl 74 arranged to engage the teeth 9 on the ratchet wheel 7, as indicated in FIGS. 15a, 15b, 15c, whereby the pivoting of the pivotable body 78 provides a rotation of the ratchet wheel 7. A second pawl mechanism 72, 84 is provided to prevent rotation of the ratchet wheel 7 in the opposite direction, again as shown in FIGS. 15a-15c.

The displacement of the pawl 74 between the two positions indicated in FIGS. 15a and 15b is provided by the reduction of the length of the twisted strings 35 by rotation of the motor and the displacement in the opposite direction is provided by the spring 40 during extension of the twisted strings 35 provided by rotation of the motor in the opposite direction, whereafter further rotation in this direction again reduces the length of the twisted strings 35, whereby a complete cycle of rotation in one direction of the motor provides a movement of the pivotable body from the position shown in FIG. 15a to the position shown in FIG. 15b and back to the position shown in FIG. 15a, this movement being provided by the twisted strings 35 being untwisted and twisted in the opposite direction during rotation of the motor in one direction. Thus, the rotation of the motor in one direction of rotation provides a full stroke for the pivotable body and thus the pawl mechanism moving the ratchet wheel one step forward and the following rotation of the motor in an opposite direction of rotation provides a further full stroke of the pivotable body and the pawl mechanism.

Thus, during one cycle of rotation in one direction and the opposite direction of the electrical motor 10, the ratchet wheel 7 will be advanced by two teeth corresponding to two displacements of the pawl 74. The pivotable body 78 comprises a protuberance 78a which co-operates with two end stop contacts 85a and 85b electrically connected to the control means for controlling the reversal of the direction of rotation of the electrical motor when the protuberance 78a contacts the end stop contact 85a. Due to the fact that the twisted strings 35 can only provide a pulling force on the pivotable body 78, a spring 40 is connected to the pivotable body to provide the movement in the direction shown by the arrow in FIG. 10.

In the embodiment shown in the figures spring 40 is a coil spring, however, other types of springs, such as a rod spring could be provided for this purpose.

Figure 16:
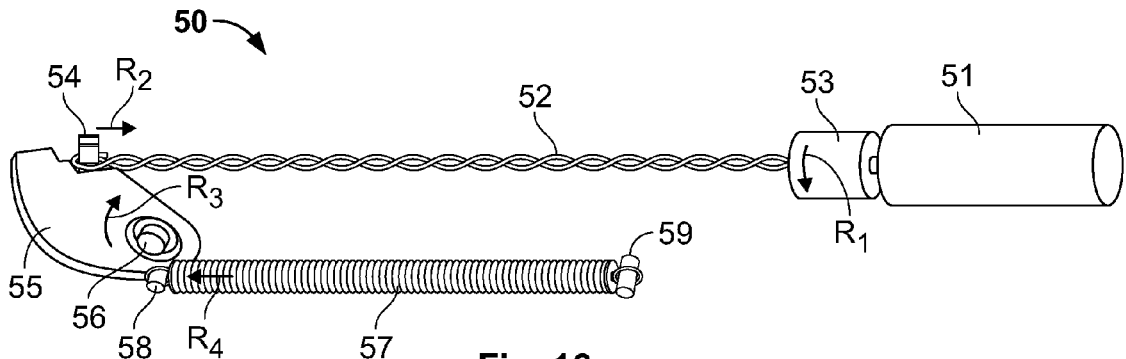
FIG. 16. is a schematic perspective view of a first embodiment of an actuator according to the invention, and FIGS. 17a-b very schematically show a second embodiment of an actuator according to the invention at two different phases of an actuation cycle.

Referring now to FIG. 16, an actuator according to the invention is referred to generally by the numeral 50 and is identical to the actuator shown in FIGS. 10-14. This actuator may be employed for any use requiring transformation of a rotation to a linear movement or a rotational force to a linear force.

A rotation motor 51 is attached to a pair of elongate, flexible elements such as strings or filaments 52 by means of a rotational body 53 that may or may not function as a fly wheel. The elements 52 are attached to a pin 54 on a pivotable plate. Rotation of the motor in the direction R1 will twist the strings 52 such that the length thereof is shortened until the pin 54 is displaced linearly in the direction R2 whereby the plate 55 is rotated around pivot 56 in the direction R3. A tension spring 57 is attached to plate 55 at pin 58 and to a not shown frame at pin 59.

Rotation of the plate 55 will expand the spring 57 in the direction R4 against the spring force thereof.

Rotation of the motor 51 in the direction opposite R1 will at first untwist the elements 52 whereby the length thereof becomes larger with the consequence that the spring 57 rotates the plate 55 in the direction opposite R3.

Further rotation of the motor 51 in the direction opposite R1 will twist the elements 52 again an eventually exert a force on said pin 54 in direction R2 again, the direction of rotation being subsequently reversed again and the cycle starts anew.

In case, a smaller interval is desired between each turn of the plate 55 in the direction R3, the motor 51 may reverse direction of rotation as soon the elements 52 have become untwisted to an extent that the spring 57 has pivoted the plate a certain distance in the direction opposite R3.

Figure 17A:
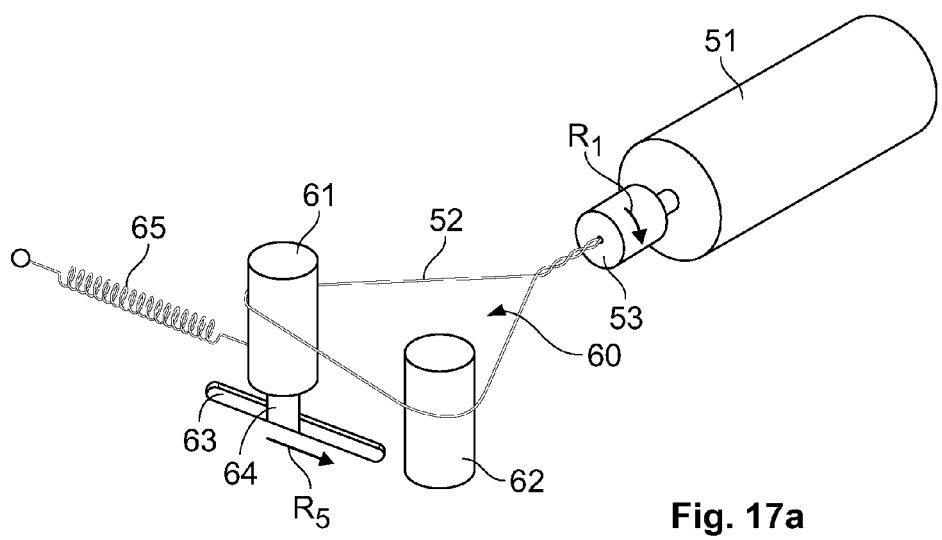
Figure 17B:
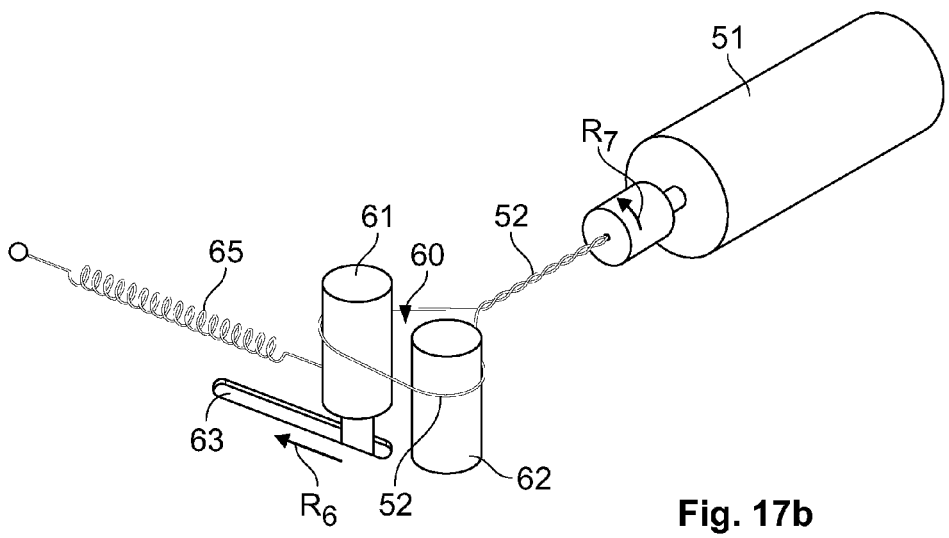

Reference is now made to FIGS. 17a-17b, where a motor 51 is attached to both opposed ends of an elongate, flexible element such as a string or filament 52 by means of a rotational body 53 that may or may not function as a fly wheel. The element 52 forms a loop 60 within which are located two bodies 61 and 62.

The body 61 is displaceable along a groove 63 in which a pin 64 of the body is slideably received. A spring 65 is attached to the displaceable body 61 such that displacement of said body 61 in the direction R5 takes place against the biasing force exerted by the spring 65.

The other body 62 is fixedly arranged such that when twisting of the element 52 by rotation of the motor 51 takes place the loop 60 is reduced in size as seen in FIG. 17b and the displaceable body 61 is forced towards the fixed body 62 along the groove 63 and against the spring force of the spring 65.

When the rotational direction of the motor is reversed so that it rotates in the direction R7, the element 52 will be untwisted, the loop 60 will enlarge and the spring 65 will displace the body in the direction R6.

Although the groove is shown extending substantially linearly, it may obviously be curved and extend at different angles to the axis of the motor.

The body 61 may be attached to a multitude of different driving or transmission mechanisms, for example the ratchet and pawl mechanisms shown in FIGS. 1-9.

A displaceable body should be taken to mean any body that can change position either by linear motion, curved motion, rotative motion, etc. and any combination thereof under the influence of a force applied to a point on or in said body.

Displacement should likewise be taken to mean any change in position resulting from linear motion, curved motion, rotative motion, etc. and any combination thereof.

What is claimed is:

1. A wearable medicine dispensing device, comprising:
   a housing that defines a cavity to receive a separate medicine-filled container such that an output end of the container is positioned away from a piston rod;
   the piston rod being arranged in the housing and being movable in a forward direction toward the medicine-filled container when the medicine-filled container is received in the cavity;
   a drive mechanism arranged in the housing to advance the piston rod in the forward direction, the drive mechanism comprising a pawl and a ratchet wheel, the pawl positioned to engage at least one of the teeth of the ratchet wheel, wherein the pawl reciprocates between a first position and a second position to incrementally rotate the ratchet wheel, wherein rotation of the ratchet wheel in a drive direction causes a linear advancement of the piston rod;
   a reversible motor coupled to the drive mechanism such that rotation of the reversible motor urges the pawl toward one of the first and second positions; and
   a battery connected to the reversible motor so as to provide power to rotate the reversible motor in a first direction and in a second reverse direction,
   wherein one cycle of rotation of the reversible motor in the first direction and in the second reverse direction cause the ratchet wheel to be advanced by one tooth corresponding to displacement of the pawl between the first and second positions.

2. The wearable medicine dispensing device of claim 1, further comprising at least two gears coupled between the reversible motor and the pawl.

3. The wearable medicine dispensing device of claim 2, further comprising a rigid plate member coupled between the at least two gears and the pawl.

4. The wearable medicine dispensing device of claim 2, wherein one or more full rotations of the rotational motor causes the pawl to pivot about an axis.

5. The wearable medicine dispensing device of claim 1, further comprising a control circuit device to repeatedly reverse the direction of rotation of the rotational motor.

6. The wearable medicine dispensing device of claim 5, further comprises a sensor that causes the rotation of the motor to be reversed from the first direction to the second reverse direction.

7. The wearable medicine dispensing device of claim 1, wherein the ratchet wheel is locked from rotation in a direction opposite to the drive direction.

8. The wearable medicine dispensing device of claim 1, wherein the ratchet wheel directly engages with the piston rod.

9. The wearable medicine dispensing device of claim 8, wherein the ratchet wheel comprises an internal thread that engages with an outward thread of the piston rod.

10. The wearable medicine dispensing device of claim 1, wherein the piston rod comprises a flexible piston rod having rod segments hinged together and outwardly threaded, wherein at least a portion of the flexible piston rod extends longitudinally in a curved configuration inside the housing.

11. The wearable medicine dispensing device of claim 1, wherein the pawl reciprocates between a retracted position and an engaged position to incrementally rotate the ratchet wheel.

12. The wearable medicine dispensing device of claim 1, wherein the drive mechanism prevents dispensation of the medicine in the event of continuous rotation of the reversible motor.

13. The wearable medicine dispensing device of claim 12, wherein the drive mechanism prevents dispensation of the medicine in the event of continuous rotation of the reversible motor so as to provide a fail-safe protection against overdosage of medicine.

14. The wearable medicine dispensing device of claim 1, further comprising a linearly displaceable plate coupled to the pawl and coupled to the reversible motor.

15. The wearable medicine dispenser device of claim 14, wherein one or more full rotations of the reversible motor causes the linearly displaceable plate to act upon the pawl.

* * * * *